United States Patent [19]

McColl et al.

[11] Patent Number: 5,041,120
[45] Date of Patent: Aug. 20, 1991

[54] MULTIPART KIT AND METHOD OF USING THE SAME TO REMOVE CEMENT USED TO SECURE PROSTHETIC JOINTS

[75] Inventors: Milton B. McColl, Los Altos Hills; Albert K. Chin, Palo Alto, both of Calif.

[73] Assignee: Origin Medsystems, Inc., San Mateo, Calif.

[21] Appl. No.: 467,724

[22] Filed: Jan. 19, 1990

[51] Int. Cl.⁵ .................. A61B 17/56; A61B 17/50
[52] U.S. Cl. ........................... 606/99; 606/100; 606/92
[58] Field of Search ............... 623/16, 18, 20, 22, 623/23, 66; 606/92, 99, 100, 94, 65, 73, 62

[56] References Cited

U.S. PATENT DOCUMENTS

| | | | |
|---|---|---|---|
| 3,915,162 | 10/1975 | Miller | 606/73 |
| 4,175,555 | 11/1979 | Herbert | 606/23 |
| 4,222,382 | 9/1980 | Antonsson et al. | 128/92 |
| 4,248,232 | 2/1981 | Engelbrecht et al. | 128/305 |
| 4,399,813 | 8/1983 | Barber | 128/92 |
| 4,463,753 | 8/1984 | Gustilo | 128/92 |
| 4,476,861 | 10/1984 | Dimakos et al. | 128/303 |
| 4,612,922 | 9/1986 | Barber | 128/92 |
| 4,686,971 | 8/1987 | Harris et al. | 128/92 |
| 4,702,236 | 10/1987 | Tarabichy | 128/92 |
| 4,834,081 | 5/1989 | Van Zile | 128/92 |
| 4,838,264 | 6/1989 | Bremer | 128/303 |
| 4,846,161 | 7/1989 | Roger | 606/99 X |

*Primary Examiner*—Danton D. DeMille
*Assistant Examiner*—Kevin G. Rooney
*Attorney, Agent, or Firm*—Limbach, Limbach & Sutton

[57] ABSTRACT

A mantle of cement having an elongate cavity formed therein is removed from adhered condition within a bone recess by successively breaking away sections of the mantle with a plurality of elongate screw threaded pulling elements proportioned to engage a limited length of a screw threaded mass of cement received in the cavity. The apparatus of the invention is provided in kit form with sufficient elements to enable the full length of the mantle to be removed in successive steps. The kit may also include a cement injection syringe and vent tube to fill the cavity of the mantle with a mass of cement, a die to form a screw threaded passage in the mass of cement, and a slap hammer connectable to the pulling elements.

15 Claims, 2 Drawing Sheets

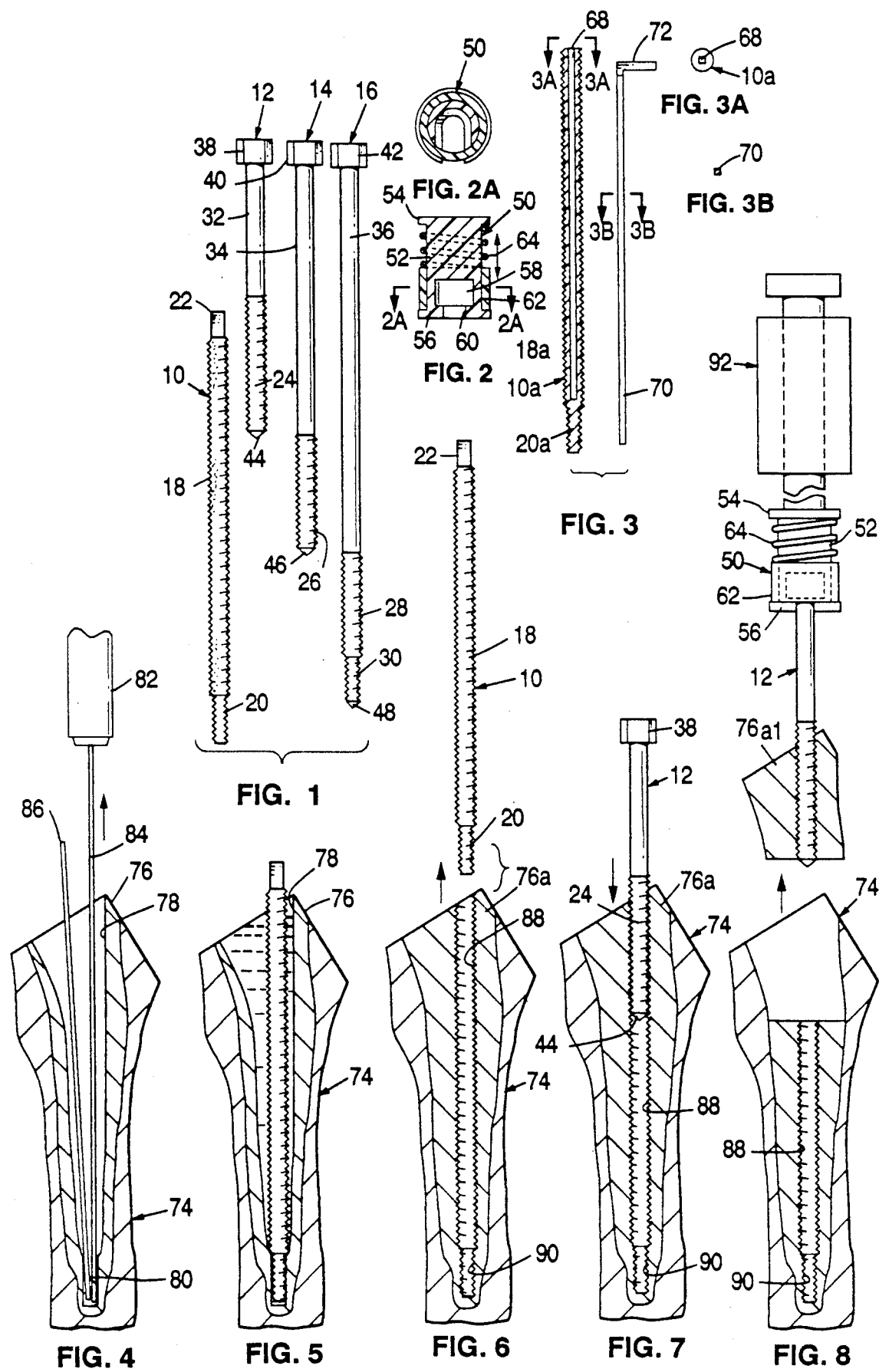

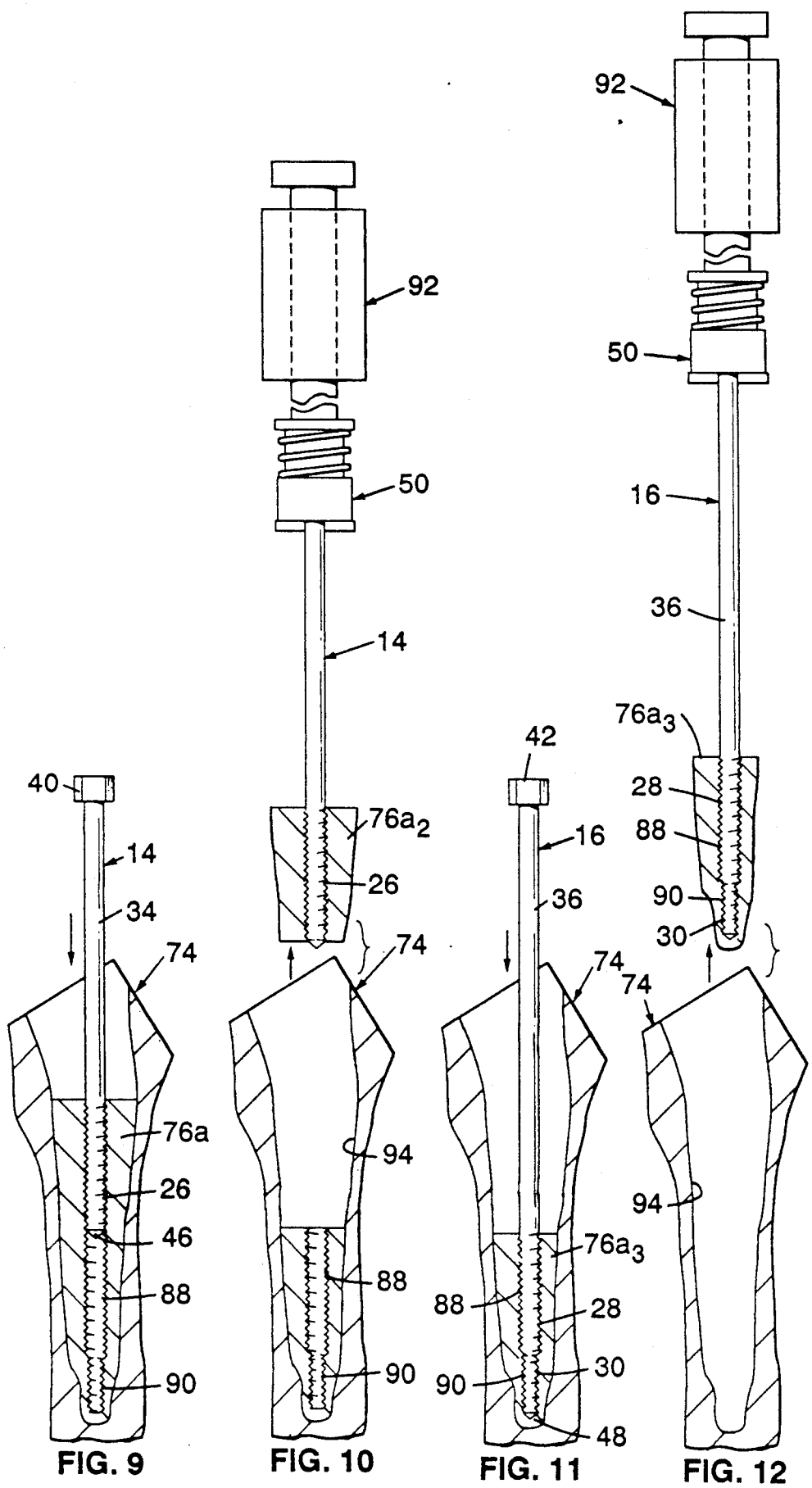

MULTIPART KIT AND METHOD OF USING THE SAME TO REMOVE CEMENT USED TO SECURE PROSTHETIC JOINTS

RELATED APPLICATIONS

This application relates to U.S. applications Ser. No. 255,650, filed Oct. 11, 1988, and Continuation-In-Part application Ser. No. 467,742 filed simultaneously herewith, both of which applications are in the name of Albert K. Chin, one of the co-inventors herein.

BACKGROUND OF THE INVENTION

Related application Ser. No. 255,650 is concerned with a method and apparatus for removing the cement mantle used to secure a prosthetic appliance within a bone cavity and, more particularly, is concerned with a technique wherein a new mass of cement is adhered in place within the mantle and a pulling tool is then employed to remove the mass and mantle as a unit. Continuation-in-part application Ser. No. 467,742 is concerned with an improvement wherein the cement mantle and newly injected mass of cement are removed in increments to avoid the severe stresses which are sometimes encountered in removing the cement mantle and newly injected mass of cement as a single unit.

The present invention is concerned with a variation of the incremental or segmental mantle removing technique of continuation-in-part application Ser. No. 467,742 and, more particularly, is concerned with a simplified and foolproof apparatus and method for carrying out that technique. In its more particular aspects, the invention is concerned with a kit of components provided to carry out the technique and an improved method which results from the employment of the kit

SUMMARY OF THE INVENTION

With the technique of the present invention, the prosthetic appliance (e.g. hip joint) is first pulled from the mantle of cement which had been used to secure it in place. A new mass of cement is then placed in the cavity in the mantle left by removal of the appliance and then a screw-threaded passage is formed in this new mass. A special die or forming tool is provided to form this screw-threaded passage while the mass is still in a soft state.

After the screw-threaded passage is formed in the new cement and the cement has hardened, the die or forming tool is removed, leaving a clean screw-threaded passage. The kit of the present invention provides a plurality of elongate pulling tools which may then be screwed into the passage to successively remove segments of the mass and the mantle secured thereto. Each pulling tool is of a predetermined length, with the first tool being of the shortest length and each successive tool being of a progressively greater length. The tools are provided with stops to limit the degree to which they may be screwed into the threaded passage, thus assuring that each tool will remove only a segment of the cement mass and adhered mantle. The final tool of the succession may be provided with a threaded distal end of a reduced diameter as compared to the threads on the other tools to facilitate its insertion into a distal section of the mantle which may have a relatively small cross-section.

In use, each successive tool removes a segment of the new cement mass and the mantle adhered thereto. It is not necessary that the segment be removed from the tool, as a new tool is provided for each successive segment. In the preferred embodiment, the tools have a bolt-like configuration and are provided with enlarged heads which may be gripped by a coupling secured to a slap hammer In order to minimize the possibility that the pulling forces applied to the tools will be other than an axial direction, the length of each successive tool is chosen so as to be no greater than necessary.

The preferred thread forming element or die takes the form of an elongate externally threaded rod which is designed so that axial pulling forces may not be applied thereto in a mistaken effort to use the die to remove the cement mantle. In one embodiment, the element or die is a plastic rod having a polygonal passage extending therethrough designed for the slidable receipt of a complemental tool designed to impart turning forces only to the element. The thread forming element or die is ideally formed or coated with a non-stick coating to facilitate its removal from the threaded passage which it is designed to create.

A principal object of the present invention is to provide an improved method and apparatus for removing the cement mantle used to secure a prosthetic appliance which is being renewed.

Another and more specific object of the invention is to provide such a method and apparatus which enables the mantle to be removed with a minimum of stress to the bone within which the mantle is adhered.

Yet another object of the invention is to provide such a method and apparatus which enables the mantle to be removed in increments, without chiseling.

Another and more specific object of the invention is to provide an improved kit which provides for the formation of an elongated threaded passage within the mantle being removed and the successive engagement of this passage with pulling tools of increasing lengths to remove the mantle in successive increments.

Still another specific object of the invention is to provide such a kit having a thread forming element or die which is designed to form the elongate threaded passage but may not be mistakenly used to apply pulling forces to the mantle.

These and other objects will become more apparent when viewed in light of the following detailed description and accompanying drawings.

BRIEF DESCRIPTION OF THE DRAWINGS

FIG. 1 is an elevational view of the kit of basic elements of the invention, including the thread forming die and three successive pulling tools;

FIG. 2 is a cross-sectional elevational view of a coupling designed to secure the pulling tools of the present invention to a slap hammer;

FIG. 2A is a cross-sectional view taken on the plane designed by Line 2A—2A of FIG. 2;

FIG. 3 is an elevational view of an alternative embodiment of the thread forming die, including the turning tool therefor;

FIG. 3A is a plane view of the thread forming die shown in FIG. 3, taken on the plane designated by Line 3A—3A;

FIG. 3B is a cross-sectional view of the turning tool, taken on the plane designated by Line 3B—3B of FIG. 3;

FIG. 4 is a cross-sectional elevational view of the upper femur of a leg, wherein the femoral component of a prosthetic hip joint has been removed from a cement mantle within the femur and a new mass of cement is in the process of being injected into the cavity left in the mantle by removal of the component;

FIG. 5 is a cross-sectional elevational view similar to FIG. 4, illustrating the step of using the thread forming die of the invention to form a threaded passage within the mass of new cement injected into the mantle;

FIG. 6 is a cross-sectional elevational view similar to FIG. 5, illustrating removal of the thread forming die from the mass of new cement to leave a threaded passage therein;

FIG. 7 is a cross-sectional elevational view similar to FIG. 6, illustrating the first of the successive pulling tools in the process of being threaded into the passage within the new cement;

FIG. 8 is a cross-sectional elevational view similar to FIG. 7, illustrating a slap hammer coupled to the first pulling tool and in the process of breaking away and removing a segment of the cement mantle from the femur;

FIG. 9 is a cross-sectional elevational view similar to FIG. 8, illustrating the second successive pulling tool in the process of being screwed into the passage in the new cement within the mantle;

FIG. 10 is a cross-sectional elevational view similar to FIG. 9, illustrating a slap hammer coupled to the second pulling tool and in the process of breaking away and removing a second segment of the mantle;

FIG. 11 is a cross-sectional elevational view similar to FIG. 10, illustrating the third successive pulling tool in the process of being screwed into the remaining cement mantle within the femur; and, FIG. 12 is a cross-sectional elevational view similar to FIG. 11, illustrating the third pulling tool coupled to a slap hammer and in the process of breaking away and removing the final segment of the cement mantle.

DESCRIPTION OF THE PREFERRED EMBODIMENTS

The kit shown in FIG. 1 includes the following components: thread forming die 10, first successive pulling tool 12, second successive pulling tool 14, and third successive pulling tool 16. The die 10 is of an elongate unitary construction and includes a main portion 18 of a uniform enlarged cross-section and a distal end portion 20 of a reduced cross-section, as compared to that of the main portion. Both the main portion 18 and distal portion 20 are threaded over their lengths with continuous screw threads of the same pitch (e.g. machine screw pitch 20). The top end of the die, designated 22, is formed with a square whereby it may be turned with a wrench. The die may be formed of metal or a polymer and ideally is provided with a non-stick external surface over the threaded portions. The non-stick surface may be a permanent integral part of the die such a TEFLON, and/or a release coating, such as DOW CORNING 20, of the Dow Corning Corporation of Midland, Mich.

The pulling tools 12, 14 and 16 are each of a bolt-like construction and fabricated of steel rod. In a typical embodiment, the tool 12 has a length of four inches, the tool 14 six inches, and the tool 16 eight inches. The main threaded sections on the tools, designated 24, 26 and 28, respectively, have a length of approximately one inch and an o.d. of $\frac{1}{4}$ inch. The screw threads on the latter sections are complemental with the threads formed by the main portion 18 of the die 10. The pulling tool 16 is formed with a distal threaded section 30 complemental with the threads formed by the end portion 20 of the die 10. The section 30 typically measures about $\frac{1}{8}$ inch in diameter and $\frac{3}{4}$ inch in length. The tools 12, 14 and 16 are formed with unthreaded sections 32, 34 and 36, respectively, above the main threaded sections thereof. These unthreaded sections have an o.d. greater than the base diameter of the main threaded sections and, thus, serve as stops to limit the degree to which the threaded sections may be threaded into place. Enlarged hexagonal heads 38, 40 and 42, respectively, are formed on the proximal ends of the tools 12, 14 and 16. These provide means whereby both torsional and pulling forces may be applied to the tools. Tapered distal tips 44, 46 and 48, respectively, are formed on the distal ends of the tools 12, 14 and 16 to facilitate their threading into a passage formed by the die 10.

The coupling shown in FIGS. 2 and 2A is designated in its entirety by the numeral 50. It comprises a main body member of a cylindrical cross-section having a reduced diameter central section 52 and enlarged end sections 54 and 56. A cylindrical cavity 58 is formed in the main body section of the coupling and proportioned for relatively snug receipt around the hexagonal heads of the pulling tools. The bottom of the coupling body is formed with a slot 60 opening through the side edge thereof for passage of the cylindrical tool sections therethrough to enable the hexagonal heads of the pulling tools to pass into the cavity 58. A sleeve 62 slidably received on the central section 52 to selectively close the side of the slot opening through the cavity 58 and thus capture the head of a pulling tool within the cavity. A compression coil spring 64 normally biases the sleeve downwardly over the slot in the side of the cavity 58, as shown in FIG. 2. The sleeve 62 may be manually lifted against the action of the spring to expose the slot.

The alternative embodiment of the thread forming die shown in FIG. 3 is designated in its entirety by the numeral 10a. The main and end portions of the die 10a correspond to those of the die 10 and are designated by the numerals 10a and 20a, respectively. The die 10a differs from the die 10 primarily in that it does not include a squared top end for engagement by a wrench, but rather includes a non-round passage 68 of a square cross-section for slidable engagement by a complemental turning tool 70. The tool 70 has an L-shaped head 72 to facilitate its turning. Because the tool 70 is proportioned for slidable receipt in the passage 68, the tool may impart torsional forces only to the die 10a. Accordingly, pulling forces cannot be applied to the die 10a through the tool 70.

DESCRIPTION OF METHOD STEPS

The use of the apparatus in carrying out the method steps is depicted sequentially in FIGS. 4 to 12. As there shown, the femur being worked upon is designated in its entirety by the numeral 74 and is illustrated after the femoral component of a prosthetic hip joint has been removed therefrom for replacement. These figures also show that the trochanter of the femur has been removed to facilitate the method.

FIG. 4 shows the femur 74 after the femoral component of the hip joint has been removed therefrom, with the cement mantle 76 which is to be removed left in place within the bone recess within the femur. As there shown, the cavity 78 within the mantle has been cleaned and a reduced diameter extension, designated 80, has been drilled into the distal end of the mantle.

The first step of the method comprises injecting cement into the cavity 78. This step is illustrated in FIG. 4 wherein an injection gun 82 is shown injecting the cement to the bottom of the cavity through a thin snout 84. A vent tube 86 is extended to the bottom of the cavity to assure that air will be vented therefrom and that the cavity will be filled to the bottom. As the cavity is filled with cement, the gun and snout are slowly retracted, as indicated by the arrow line in FIG. 4. The vent tube 86 would be withdrawn after the reduced diameter extension 80 of the cavity is adequately filled. Most typically, the mantle 76 is comprised of old methylmethacrylate cement. This type of cement is capable of being partially dissolved and softened by the application of new like fluid cement thereto. Accordingly, assuming the mantle is comprised of such cement, the new cement injected into the cavity 78 would be like cement and, ultimately, bond to the original mantle and form an integral part thereof.

FIG. 5 shows the step of forming a screw threaded passage through the newly injected soft cement within the cavity 78. As there shown, the die 10 has been screwed to essentially the bottom of the cavity to form a screw-threaded passage therein. It should also be appreciated that the die is provided with a non-stick coating prior to being so screwed into place, either in the form of an integral surface formed as part of the die and/or as a non-stick coating applied to the die.

FIG. 6 shows the mantle, now designated 76a, after the newly injected cement has cured and formed an integral mass with the mantle. As shown in FIG. 6, the die 10 has been threaded out of the mantle, leaving a passage comprised of an enlarged proximal portion 88 and a reduced diameter distal portion 90.

FIG. 7 shows the first pulling tool 12 being threaded into engagement with the upper section of the proximal portion 88. As there shown, the tool is threaded into place to approximately the maximum extent permitted by the section 32 thereof.

FIG. 8 shows the tool 12 connected to a slap hammer 92 through the coupling 50. As there shown, pulling force has been applied to the upper portion of the mantle 76a through the slap hammer and that portion or segment, designated 76a$_1$ has been removed from the femur 74. Such removal is possible because the methylmethacrylate cement has very little tensile strength and readily fractures upon being subjected to tensile force by the slap hammer.

FIG. 9 shows the step of screwing the second pulling tool 14 into the portion of the mantle 76a remaining after removal of the segment 76a$_1$. As there shown, the tool is fully threaded into place with the section 34 serving as a stop to limit the degree to which the tool may penetrate the threaded passage in the mantle.

FIG. 10 shows the slap hammer 92 connected to the tool 14 through the coupling 50 and a segment 76a$_2$ as having been removed from the femur by operation of the slap hammer. Again, it should be appreciated that the low tensile strength of the methylmethacrylate cement enables the segment 76a$_2$ to be fractured away from the portion of the mantle remaining in the recess 94 within the femur.

FIG. 11 shows the third tool 16 as it is being threaded into the remaining portion of the mantle, designed 76a$_3$, within the recess 94. As there shown, the distal threaded section 30 of the tool is threaded fully into the distal portion 90 of the threaded passage and the main threaded section 28 is threaded into the proximal portion 88 of the passage.

FIG. 12 shows the final step of removing the mantle segment 76a$_3$ from the recess 94 through means of a slap hammer 92 connected to the tool 14 by the coupling 50. The remaining recess 94 has the mantle fully removed therefrom and is ready for renewal to receive a new femoral prosthesis.

CONCLUSION

From the foregoing description, it will be apparent that the present invention provides a simplified and foolproof apparatus and method for removing a cement mantle from a bone recess. The mantle is removed in segments, without the requirement that the various removal tools be reused. Stresses on the bone are minimized.

While preferred embodiments of the invention have been illustrated and described, it should be understood that the invention is not intended to be limited to the specifics of these embodiments, but rather is defined by the accompanying claims.

What is claimed is:

1. A kit for removing a mantle of cement having an elongate cavity formed therein from adhered condition within a bone recess, said kit comprising:
   (a) a die for forming an elongate screw threaded passage within a mass of cement injected into the cavity;
   (b) a first elongate element of a predetermined length, said element having a screw threaded section complemental with a screw threaded passage formed by the die;
   (c) a second elongate element of a predetermined length greater than that of the first element, said second element having a screw threaded section complemental with a screw threaded passage formed by the die;
   (d) torque transmitting means on said first and second elements to enable said elements to be screwed into threaded engagement with a threaded passage formed in a mass of cement by the die;
   (e) stop means operatively associated with the screw threaded sections of the first and second elements to limit the extent of threaded engagement of said sections with the passage to less than the full length of the passage whereby the first element is restricted to engaging less than the full length of the passage and, after removal of a threaded section of cement by the first element, the second element may threadably engage a successive section of the passage;
   (f) gripable means on said first and second elements to enable pulling forces to be applied thereto to remove a mass of cement threadably engaged by the screw threaded sections of the elements from a bone recess; and,
   (g) a slap-hammer engageable with the gripable means to impart pulling forces thereto.

2. A kit according to claim 1 wherein:
   (a) the first and second elongate elements comprise cylindrical shafts;
   (b) the screw threaded sections of said elements take the form of machine screw threads formed on said shafts and having a base diameter less than the diameter of the shafts;
   (c) the machine screw threads terminate intermediate the length of said shafts; and, (d) the stop means are provided by portions of the shafts adjacent the screw threaded sections having a diameter greater than the base diameter of the screw threads.

3. A kit according to claim 2 wherein the gripable means comprise a head formed on the shaft of each of the elongate elements, each said head having a cross-section greater than that of the shaft upon which it is formed.

4. A kit according to claim 1 wherein the die comprises an elongate shaft having machine screw threads formed on the exterior thereof.

5. A kit according to claim 4 wherein the threads of the die have a non-stick surface.

6. A kit according to claim 5 wherein the shaft of the die has an elongate bore opening through one end thereof, said bore having a non-round cross-section and being slidably engageable by a tool of a complemental cross-section.

7. A kit according to claim 1 wherein the elongate elements are of a relatively narrow cross-section over the majority of the length thereof and the gripable means comprise heads formed on the elongate elements of an enlarged cross-section as compared to said narrow cross-section, said kit further comprising a coupling secured to the slap hammer for releasably securing the hammer to the head of an elongate element, said coupling comprising:
  (a) a body having a cavity therein proportioned to receive and capture the head of an elongate element, said body having a slot opening through a side thereof and into said cavity of a width greater than the narrow cross-section of the elongate elements and less than the enlarged cross-section of the heads; and,
  (b) a sleeve slidably received on the body to selectively close the slot.

8. A kit according to claim 7, further comprising biasing means to normally urge the sleeve to the condition closing the slot.

9. A kit according to claim 1 further comprising a syringe for injecting a mass of cement into the cavity in the mantle of cement.

10. A kit according to claim 9 further comprising a tube for venting the cavity as cement is being injected thereinto.

11. A method for removing a mantle of cement having an elongate cavity formed therein from adhered condition within a bone recess, said method comprising:
  (a) injecting a mass of cement into the cavity;
  (b) forming a screw threaded passage in the mass of cement and permitting the mass of cement to cure and bond to the mantle of cement;
  (c) providing a first elongate element of a predetermined length having a screw threaded section proportioned for complemental engagement with the screw threaded passage and a stop to limit engagement of the screw threaded section thereof to less than the full length of the passage;
  (d) providing a second elongate element of a predetermined length greater than that of the first element having a screw threaded section proportioned for complemental engagement with the screw threaded passage;
  (e) threadably engaging the first element with the passage to the extent permitted by the stop and applying pulling force to the first element to break away and remove the cement mass engaged thereby, together with the mantle bonded to the mass of removed cement; and,
  (f) threadably engaging the second element with the passage and applying pulling force to the second element to break away and remove the cement mass engaged thereby, together with the mantle bonded to the mass of removed cement.

12. A kit for removing a mantle of cement having an elongate cavity formed therein from adhered condition within a bone recess, said kit comprising:
  (a) a die comprising an elongate shift having a main portion of a uniform enlarged cross-section and a distal end portion of a uniform reduced cross-section as compared to that of the main portion. said die having screw threads of the same pitch formed over both the main and distal portions for forming an elongate screw threaded passage within a mass of cement injected into the cavity;
  (b) a first elongate element of a predetermined length, said element having a screw threaded section complemental with a screw threaded passage formed by the die;
  (c) a second elongate element of a predetermined length greater than that of the first element, said second element having a screw threaded section complemental with a screw threaded passage formed by the die;
  (d) torque transmitting means on said first and second elements to enable said elements to be screwed into threaded engagement with a threaded passage formed in a mass of cement by the die;
  (e) stop means operatively associated with the screw threaded sections of the first and second elements to limit the extent of threaded engagement of said sections with the passage to less than the full length of the passage whereby the first element is restricted to engaging less than the full length of the passage and, after removal of a threaded section of cement by the first element, the second element may threadably engage a successive section of the passage; and,
  (f) gripable means on said first and second elements to enable pulling forces to be applied thereto to remove a mass of cement threadably engaged by the screw threaded sections of the elements from a bone recess.

13. A kit according to claim 12 wherein the screw threaded section of the second elongate element comprises a proximal portion of a uniform enlarged cross-section for complemental engagement with a screw thread formed by the main portion of the die and a distal portion of a uniform reduced cross-section for complemental engagement with a screw thread formed by the distal end part of the die.

14. A kit for removing a mantle of cement having an elongate cavity formed therein from adhered condition within a bone recess, said kit comprising:
  (a) a die for forming an elongate screw threaded passage within a mass of cement injected into the cavity;
  (b) a first elongate element of a predetermined length. said element having a screw threaded section complemental with a screw threaded passage formed by the die;
  (c) a second elongate element of a predetermined length greater than that of the first element, said second element having a screw threaded section complemental with a screw threaded passage formed by the die;

(d) torque transmitting means on said first and second elements to enable said elements to be screwed into threaded engagement with a threaded passage formed in a mass of cement by the die;

(e) stop means operatively associated with the screw threaded sections of the first and second elements to limit the extent of threaded engagement of said sections with the passage to less than the full length of the passage whereby the first element is restricted to engaging less than the full length of the passage and, after removal of a threaded section of cement by the first element, the second element may threadably engage a successive section of the passage;

(f) gripable means on said first and second elements to enable pulling forces to be applied thereto to remove a mass of cement threadably engaged by the screw threaded sections of the elements from a bone recess; and, (g) a syringe for injecting a mass of cement into the cavity in the mantle of cement.

15. A method for removing a mantle of cement having an elongate cavity formed therein from adhered condition within a bone recess, said method comprising:

(a) injecting a new mass of cement into the cavity to provide an integral body of hardened cement comprised of the mantle and the new mass of cement;

(b) providing an elongate passage in the body of hardened cement;

(c) providing a first elongate element having a portion proportioned for complemental gripping engagement with the passage and a stop to limit engagement of the portion to less than the full length of the passage;

(d) providing a second elongate element having a portion proportioned for complemental gripping engagement with the passage;

(e) engagement the first element with the passage to the extent permitted by the stop and applying pulling force to the first element to break away and remove the body of hardened cement engaged thereby; and, (f) engaging the second element with the passage and applying pulling force to the second element to break away and remove the body of hardened cement engaged thereby.

* * * * *

UNITED STATES PATENT AND TRADEMARK OFFICE
CERTIFICATE OF CORRECTION

PATENT NO. : 5,041,120

DATED : August 20, 1991

INVENTOR(S) : Milton B. McColl and Albert K. Chin

It is certified that error appears in the above - identified patent and that said Letters Patent is hereby corrected as shown below:

<u>In the Claims</u>:

In column 8, line 11 of Claim 12, delete "shift" and insert --shaft--

In column 10, line 17 of Claim 15, delete "engagement" and insert --engaging--

Signed and Sealed this

Twelfth Day of January, 1993

Attest:

DOUGLAS B. COMER

*Attesting Officer*　　*Acting Commissioner of Patents and Trademarks*